United States Patent [19]  
Halpern et al.

[11] Patent Number: 4,478,998  
[45] Date of Patent: Oct. 23, 1984

[54] PROCESS FOR PREPARING AMINE SALTS OF PHOSPHORIC ACIDS

[75] Inventors: Yuval Halpern, Skokie; Donna M. Mott, Des Plaines, both of Ill.; Ron H. Niswander, Lake Jackson, Tex.

[73] Assignee: Borg-Warner Chemicals, Inc., Parkersburg, W. Va.

[21] Appl. No.: 497,354

[22] Filed: May 23, 1983

[51] Int. Cl.$^3$ .................. C07D 251/70; C07D 251/46; C07F 9/65; C07F 9/15
[52] U.S. Cl. .................................... 544/195; 260/974; 260/927 R
[58] Field of Search ................... 544/195; 260/927 R, 260/974

[56] References Cited

U.S. PATENT DOCUMENTS

| | | | |
|---|---|---|---|
| 3,936,416 | 2/1976 | Brady | 260/42.18 |
| 4,154,930 | 5/1979 | Halpern | 544/195 |
| 4,201,705 | 5/1980 | Halpern et al. | 260/45.8 NT |
| 4,253,972 | 3/1981 | Fleenor | 260/45.8 NT |
| 4,373,103 | 2/1983 | Jung et al. | 544/195 |

Primary Examiner—John M. Ford  
Attorney, Agent, or Firm—Robert L. Zieg

[57] ABSTRACT

A process for preparing amino-s-triazine salts of bis-(pentaerythritol phosphate) phosphoric acid. The process involves reacting the particular amine with the corresponding acid chloride, i.e., the phosphorous oxychloride, in the presence of water. The salts are effective flame-retardants in a number of different types of polymers.

7 Claims, No Drawings

PROCESS FOR PREPARING AMINE SALTS OF PHOSPHORIC ACIDS

This invention relates to the preparation of certain amine salts of organic phosphoric acids. More particularly, it relates to a process involving the reaction of a polyamine such as melamine with an acid chloride of a complex organic phosphoric acid. The amine salts are useful as flame-retardant additives in certain polymer compositions.

BACKGROUND OF THE INVENTION

Polymers vary widely in their resistance to burning. Some, such as the polyolefins, polystyrene, polyalkyl acrylates and methacrylates, and the like, burn readily. Polytetrafluoroethylene, polyvinylidene chloride and polyvinyl chloride, on the other hand, have a rather high resistance to burning. In any event, it obviously is highly desirable that, for certain applications, a polymer should have a high degree of flame retardance so that it will meet the requirements of various building codes or that it will meet safety standards imposed on toys, carpeting, drapery materials, automotive applications, etc.

The treatment of these more flammable polymers to increase their resistance to burning is well known; such treatment generally has involved the incorporation in the polymer composition of substantial proportions of antimony oxide, halogenated hydrocarbons and low molecular weight phosphate esters. Ordinarily, though, the effective use of these and other additives has required their presence in such high concentrations as to adversely affect the desirable properties of the polymer. Thus, such desirable properties as hardness, clarity, strength, elasticity, etc., are diminished significantly by the presence of large amounts of a flame-retardant chemical.

An alternative approach is to incorporate char-forming additives which, in the presence of flame, form a thick, non-flammable insulating barrier to protect the substrate polymer. One such intumescent or char-forming system, disclosed in U.S. Pat. No. 3,936,416, employs a combination of melamine pyrophosphate and a polyol. This additive combination is effective in providing a non-burning, non-dripping polypropylene composition. Preparation and compounding with these materials can be difficult. During preparation, however, the additive combination must be degassed in order to avoid foaming during the compounding with polypropylene and/or in subsequent molding operations. In addition, the additive as obtained has a substantial tan or brown color which imparts an undesirable hue to the polypropylene compositions, and the additive is obtained as a hard, solid mass which is pulverized with some difficulty for compounding.

The pentate, i.e., pentaerythritol diphosphate, salts of amino-s-triazines are effective intumescent flame retardant additives for polyolefins, providing compositions that are self-extinguishing, intumescent and non-dripping. The additives are dry, white, powdery solids and are readily compounded with polyolefins to provide compositions which have excellent color and which are readily processed without apparent foaming or decomposition. The preparation of these compounds is disclosed in U.S. Pat. No. 4,154,930, and their use in polyolefin compositions is disclosed in U.S. Pat. No. 4,201,705 and U.S. Pat. No. 4,253,972.

The preparation of these pentate salts is accomplished by the reaction of dichloropentate, melamine and water. A mixture of these three is heated briefly to cause formation of the desired salt. The salt product is said to be particularly useful as a flame-retardant additive in polymers when used in combination with a polyol such as pentaerythritol.

SUMMARY OF THE INVENTION

The invention of the present application is a process for the preparation of an amino-s-triazine salt of a phosphoric acid, said salt having the structure:

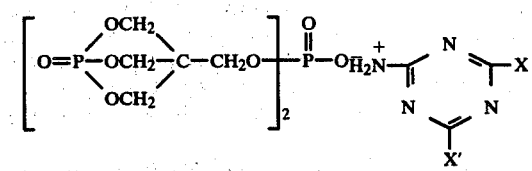

where X and X' are the same or different hydroxy or amine groups comprising reacting the acid chloride of such acid with an amino-s-triazine of the structure:

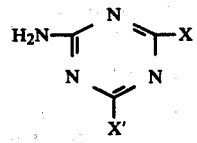

in the presence of water. Such salts are effective intumescent flame-retardant additives for several polymers, providing compositions that are self-extinguishing, intumescent and non-dripping. The salts are white, powdery solids, readily compoundable with polymers to give flame-retarded compositions which have excellent color and which are easily processed without foaming or decomposing during molding.

DETAILED DESCRIPTION OF THE INVENTION

The structural formula shown above represents bis-(pentaerythritol phosphate) phosphoric acid. The acid chloride from which it is derived is called bis-(pentaerythritol phosphate) phosphorous oxychloride. It is prepared by the reaction of pentaerythritol phosphate with phosphorus oxychloride. The

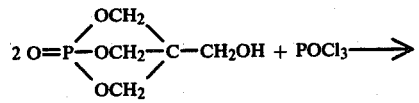

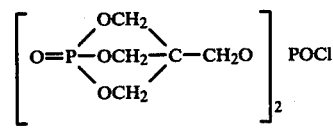

reaction is carried out by warming a mixture of the two reactants, usually in a solvent such as acetonitrile.

The process of the present invention involves two successive reactions, viz., conversion of the bis-(pentaerythritol phosphate) phosphorus oxychloride to the corresponding phosphoric acid, and neutralization of this acid with an amino-s-triazine. It is not necessary, however, to isolate the intermediate acid. The acid chloride, water and amino-s-triazine are mixed at elevated temperature, i.e., from about 50° C. to about 105° C., cooled and filtered. The crystalline precipitate is the desired amine salt.

A preferred way of carrying out the reaction involves using freshly prepared bis-(pentaerythritol phosphate) phosphorus oxychloride as it is obtained directly from its preparation from pentaerythritol phosphate and phosphorus oxychloride. Thus, in a typical instance, pentaerythritol phosphate is reacted with phosphorus oxychloride yielding, after evaporation of the solvent, a white solid. To this solid is added melamine and boiling water and the desired product results. The latter reaction requires equimolar quantities of acid chloride, water and amine, although larger amounts of water are invariably used. Likewise, in some instances it may be desirable to us an excess either of the acid chloride or amine.

The reaction of pentaerythritol phosphate with phosphorus oxychloride, on the other hand requires two mols of pentaerythritol phosphate per mol of phosphorus oxychloride.

The amino-s-triazine preferably is melamine, i.e., 1.3.5-triamino-s-triazine. Other contemplated amines include ammelide and ammelin.

The process is illustrated by the following example.

EXAMPLE

A solution of 24 g. (0.132 mol) of pentaerythritol phosphate and 6 ml. (0.066 mol) of phosphorus oxychloride in 100 ml. of acetonitrile is heated at reflux temperature. The hydrogen chloride which is evolved is trapped with an aqueous sodium hydroxide bubbler. During the reaction all is in solution. After two hours, the product mixture is evaporated to dryness yielding a white powder. $C^{13}$NMR analysis shows the presence of greater than 90% of the desired bis-(pentaerythritol phosphate) phosphorous oxychloride, with the rest being the related mono- and tris- derivatives.

To this white powder there is added with stirring, 7.56 g. (0.06 mol) of melamine and 150 ml. of boiling water. After five minutes of continued stirring the hot solution is filtered and the filtrate is cooled. A white precipitate crystallizes from solution, and is collected on a filter. Yield: 23 g., 70% of the theory (overall). Elemental analyses show the following:

| Element | Theory | Found | |
|---------|--------|-------|------|
| C | 16.97% | 16.24 | 0.2% |
| Cl | 0 | 0.05 | 0.1% | which corresponds substantially to that of the desired mono-melamine salt. $C^{13}$NMR analysis and IR analysis confirm that identification.

Similarly, the ammelin and ammelide salts can be prepared by substitution of these amines for melamine in the above procedure.

The normally flammable polymers which are susceptible to improved flame-retardant properties by means of the amine salts herein include olefin polymers such as polypropylene, polyethylene, polybutadiene, ethylene-propylene copolymers, EPDM polymers, polyisobutylene, etc.; polystyrene and polyacrylates and polymethylacrylates such as polymethyl methacrylate, polymethyl acrylate, polybutyl methacrylate, etc. Combinations of these likewise are contemplated.

The above amine salts may suitably be added to any of these normally flammable polymers in amount sufficient to give the desired degree of flame retardation. The amount required to give a desirable flame-retardant polymer varies widely depending upon the particular polymer, the shape of the polymer in its final form and the degree of flame retardation desired. The flame-retarded compositions herein contain a flame-retarding amount of the additive. By "flame-retarding amount" is meant that amount which when present in the polymer measurably reduces the tendency of the polymer to burn. They may contain up to about 50% of such additives. In the preferred compositions the combined additive will comprise from about 20% to about 50% of the composition. In most instances, because of the relative cost and effectiveness, the compositions will contain from about 20% to about 40% of the additive.

The polymer compositions for which data is set out in the table below each contain 100 parts of the indicated polymer and the indicated amount of the mono-melamine salt of bis-(pentaerythritol phosphate) phosphoric acid as prepared in the above Example.

Preparation of the flame-retardant compositions of this invention is best accomplished by mixing them in an electrically heated Brabender head for about 10 minutes at 200° C. and 60 rpm. The test specimens for which data is shown in the tables are prepared from compression molded slabs.

The flame retardance of a plastic material can be determined by means of Underwriters Laboratories Test UL-94. The test specimen measures 5"×0.5"×0.125"; it is suspended vertically at a measured height above the flame from a Bunsen burner. After 10 seconds the flame is removed and the duration of the flaming of the test specimen is noted. Immediately, the flame is placed again under the specimen and after 10 seconds the flame again is withdrawn and the duration of flaming and glowing is noted. Five test specimens are thus tested and the results of all five tests are considered in the determination of a rating for the plastic material.

The following are noted: (1) duration of flaming after first flame application; (2) duration of flaming after second flame application; (3) duration of flaming plus glowing after second flame application; (4) whether or not specimens burn up to their point of suspension; and (5) whether or not specimens drip flaming particles which ignite a cotton swatch placed 12 inches beneath the test specimen. The highest rating given to a material is "V-0". It indicates that (1) no specimen burns with flaming combustion for more than 10 seconds after each application of the test flame; (2) the material does not have a flaming combustion time exceeding 50 seconds for the 10 flame applications for each set of 5 specimens; (3) no specimen burns with flaming or glowing combustion up to the holding clamp; (4) no specimen drips flaming particles that ignite the dry cotton beneath the specimen; and (5) no specimen glows for more than 30 seconds after the second removal of the flame.

The next highest rating is "V-1". It indicates that (1) no specimen burns with flaming combustion for more than 30 seconds after each application of the test flame; (2) the material does not have a flaming combustion time exceeding 250 seconds for the 10 flame applications for each set of 5 specimens; (3) no specimen burns with flaming or glowing combustion up to the holding clamp; (4) no specimen drips flaming particles that ignite the dry surgical cotton beneath the specimen; and (5) no specimen glows for more than 60 seconds after the second removal of the flame.

A "V-2" rating is given to a composition (1) when no specimen burns with flaming combustion for more than 30 seconds after each application of the test flame; (2) it does not have a total flaming combustion time exceeding 250 seconds for the 10 flame applications for each set of 5 specimens; (3) no specimen burns with flaming or glowing combustion up to the holding clamp; (4) some specimens drip flaming particles which burn only briefly, some of which ignite the dry cotton beneath the specimen; and (5) no specimen glows for more than 60 seconds after the second removal of the flame.

The lowest rating given to a material in this test is "NSE" ("non-self-extinguishing"). It indicates that the material has failed to meet one or more of the criteria for the UL-94 vertical test.

Another test for the flammability of a plastic material measures the minimum concentration of oxygen that will just support combustion. The test is an ASTM test, D 2863-70. It is carried out in a glass column wherein the concentration of oxygen is varied until that concentration is found which will just support the burning of a test specimen, for 3 minutes or until 50 mm of the specimen has burned. The test specimen is 70–150 mm long by 6.5 mm wide by 3.0 mm thick. This concentration of oxygen is called the oxygen index. A high oxygen index indicates a highly flame-retardant specimen (O.I.).

The effectiveness of the products herein as flame-retardant additives in polymer compositions is shown in the table below.

TABLE

| Polymer | Product of Ex. (%) | UL-94 | O.I. |
| --- | --- | --- | --- |
| Polypropylene | 0 | NSE | 17.5 |
| Polypropylene | 23.1 | V-O | 31.7 |
| Polypropylene | 20.0 | V-O | 27.5 |
| Polymethyl methacrylate | 0 | NSE | 17.3 |
| Polymethyl methacrylate | 28.6 | V-O | 33.0 |
| Polystyrene | 0 | NSE | 18.3 |
| Polystyrene | 31.0 | V-O | 27.0 |

All parts and percentages herein, unless otherwise expressly stated, are by weight.

We claim:

1. A process for the preparation of an amino-s-triazine salt of a phosphoric acid having the structure

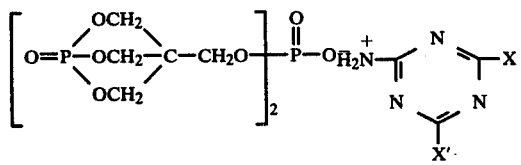

where X and X' are the same or different hydroxy or amine groups comprising reacting the acid chloride of bis-(pentaerythritol phosphate) phosphoric acid with an amino-s-triazine of the structure

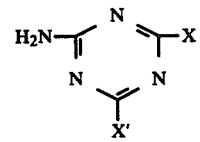

in the presence of water.

2. The process of claim 1 wherein the amino-s-triazine is melamine.

3. The process of claim 1 wherein substantially equimolar quantities of acid chloride and amino-s-triazine are used.

4. The process of claim 1 wherein a solvent is used to dissolve the reaction mixture.

5. The process of claim 1 wherein the temperature is within the range of from about 50° C. to about 105° C.

6. The process of claim 4 wherein the solvent is water.

7. The process of claim 1 wherein the acid chloride reactant, viz.,

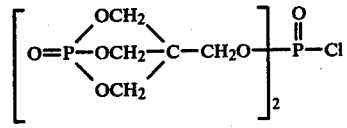

is prepared by the reaction of pentaerythritol phosphate with phosphorus oxychloride.

* * * * *

UNITED STATES PATENT AND TRADEMARK OFFICE
CERTIFICATE OF CORRECTION

PATENT NO. : 4,478,998
DATED : October 23, 1984
INVENTOR(S) : Yuval Halpern, Donna M. Mott and Ron H. Niswander It is certified that error appears in the above—identified patent and that said Letters Patent is hereby corrected as shown below:

Column 2, line 15, substitute the structure now appearing in the patent, for the correct structure as shown below.

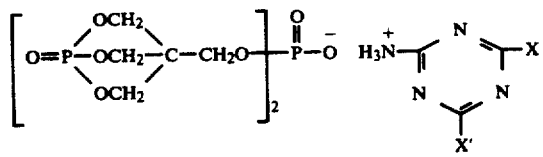

Column 6, line 3 of Claim 1, substitute the structure now appearing in the patent, for the correct structure as shown below.

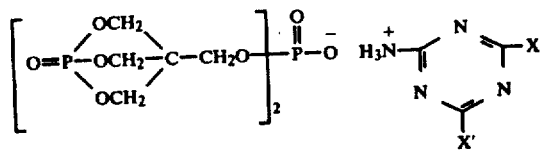

Signed and Sealed this

Second Day of April 1985

[SEAL]

Attest:

DONALD J. QUIGG

Attesting Officer        Acting Commissioner of Patents and Trademarks